(12) United States Patent
Aita

(10) Patent No.: US 6,642,512 B2
(45) Date of Patent: Nov. 4, 2003

(54) FOCUSED ION BEAM APPARATUS

(75) Inventor: Kazuo Aita, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 10/055,292

(22) Filed: Jan. 23, 2002

(65) Prior Publication Data

US 2002/0100871 A1 Aug. 1, 2002

(30) Foreign Application Priority Data

Jan. 24, 2001 (JP) .................................... 2001-016296

(51) Int. Cl.$^7$ ................................................ H01S 1/00

(52) U.S. Cl. ...................................... 250/251; 250/309

(58) Field of Search ................................ 250/251, 305, 250/310

(56) References Cited

U.S. PATENT DOCUMENTS 5,990,476 A * 11/1999 Larson et al. ............... 250/251

* cited by examiner

Primary Examiner—John R. Lee
Assistant Examiner—Phillip A Johnston
(74) Attorney, Agent, or Firm—Adams & Wilks

(57) ABSTRACT

The present invention achieves the quick and precise neutralization operation for wide area charge up and limited area charge up, both existing in a sample in a mixed manner at the same time, by having charge neutralizers separately provided for wide area charge up and limited area charge up respectively, or by having a charge neutralizer with a scanning function, so that a beam can be scanned or stopped at the perceived area by a deflector, or having a charge neutralizer with an iris having a central opening and openings in the periphery of the central opening within the optical system, so that a quick and precise neutralization operation can be achieved with respect to wide area charge up and limited area charge up both existing in a sample in a mixed manner at the same time.

14 Claims, 4 Drawing Sheets

FOCUSED ION BEAM APPARATUS

BACKGROUND OF THE INVENTION

This invention relates to a technique for a charge neutralizer for neutralizing electric charge caused by ion irradiation during sample observation with a scanning ion microscope.

The basic configuration of a focused ion beam device is shown in FIG. 6. Reference numeral 1 denotes a liquid metal ion source, 3 is a ion optical system for producing a focused ion beam 2, and 4 is a deflector for deflection scanning of the focused ion beam 2. When the ion beam is irradiated on a sample 9 placed on a sample stage 7, secondary charged particles such as electrons or ions are caused to be ejected from the irradiated part. Reference numeral 5 denotes a secondary charged particle detector which captures and detects the secondary charged particles. The detection signal can be input to a computer 10, where correspondence to the beam scanning position is checked and shown on the display 11 as a scanning ion microscope image. The focused ion beam device not only has a function as a scanning ion microscope, but also a maskless etching function and a maskless deposition function realized by irradiating the focused ion beam, but gas assist etching is also realized by irradiating the ion beam by spraying assist gas, such as a halogen, from a gas gun 6, and deposition can be performed, in which a film is formed on the surface of the sample by irradiating the ion beam by spraying material gas from the gas gun 6.

When the beam of charged particles such as ions is irradiated on the sample surface, the charge of the charged particle is injected into the sample. The sample then radiates the secondary charged particles, and takes a differential charge. Generally, this phenomenon is called charge-up. Depending on the charge-up conditions on the sample surface, the amount of radiated secondary charged particles due to the beam irradiation changes. For example, suppose that the beam of charged particles is the focused ion beam carrying the positive charge, and the sample surface is charged-up with a positive charge by irradiating the ion beam on the sample surface. Then, the potential of the sample surface increases and has the effect of holding the negative secondary electrons carrying negative charge discharged from the sample surface. On the contrary, when the secondary ion carries positive charge, it has a repulsion effect and makes discharge easy. As a result, this charge-up phenomenon is deemed undesirable in the scanning microscope field, where secondary electrons or secondary ions are detected to derive the surface image, because the amount of the radiated secondary charged particles is affected by the physical conditions due to the charge-up of the surface, which has no relation to the material or shape of the sample surface. Also another problem arises in the case where the sample or the area near the area where electrons are irradiated is asymmetrical in terms of electrical resistance, in that the path of the irradiated beam is affected, and causes beam drift.

Reference numeral 8 of the focused ion beam device shown in FIG. 6 represents a charge neutralizer, which is capable of neutralizing electric charge by irradiating electrons to the sample 9, which takes positive charge. However, there are variations in the charged state of the sample surface, which means that the neutralization of the electrical charge will not always be easy even when utilizing this charge neutralizer 8. Another state of electrical charge is shown in FIGS. 1A and 1B. As int he case of FIG. 1A, where the sample surface is equally charged, irradiation can be performed in a wide range as making an electron shower. But in the case of FIG. 1B, where an isolated pattern made of a material with different resistance on the insulation sample is charged in a limited area, which cannot be neutralized by the irradiation in an electron shower manner. It is therefore effective to focus the electrons to make a beam to irradiate the limited area. Devices are becoming more precise recently, and when observing defective parts of a device using a microscope, neutralization of the electrical charge of the limited area is required. If there is only one form of electrical charge of the sample, it can be dealt with, however, when a phenomenon of electrical charge over a wide area and a phenomenon of electrical charge in a limited area occur at the same time, a charge neutralizer should be adjusted and switched so as to be capable of wide range irradiation or capable of limited area irradiation. However, this switching operation is not only troublesome, but also the response against the switching operation is slow. Namely, it takes a while for the new manner of irradiation to reach a stable state form the switched timing, and the problem arises that it cannot cope with the phenomena.

SUMMARY OF THE INVENTION

The purpose of the present invention is to provide a focused ion beam device, having one or a plurality of charge neutralizers, which is capable of achieving a quick and precise neutralization operation for electrical charge over a wide area and electrical charge in a limited area, when both situations exist in the sample in a mixed manner.

The present invention achieves a quick and precise neutralization operaiton for charge up over wide area and charge up in a limited area, when both exist within the sample in a mixed manner, by having a charge neutralizer with a function for neutralizing electrical charge, separately provided for charge up over a wide area and for charge up in a limited area, or by having a charge neutralizer with a scanning function, to scam a beam or to stop at the prescribed area using a deflector, or by having a charge neutralizer with an iris, having a central opening a plurality of openings in the periphery of the central opening, within an optical system.

DETAILED DESCRIPTION OF THE INVENTION

Figure 1B:
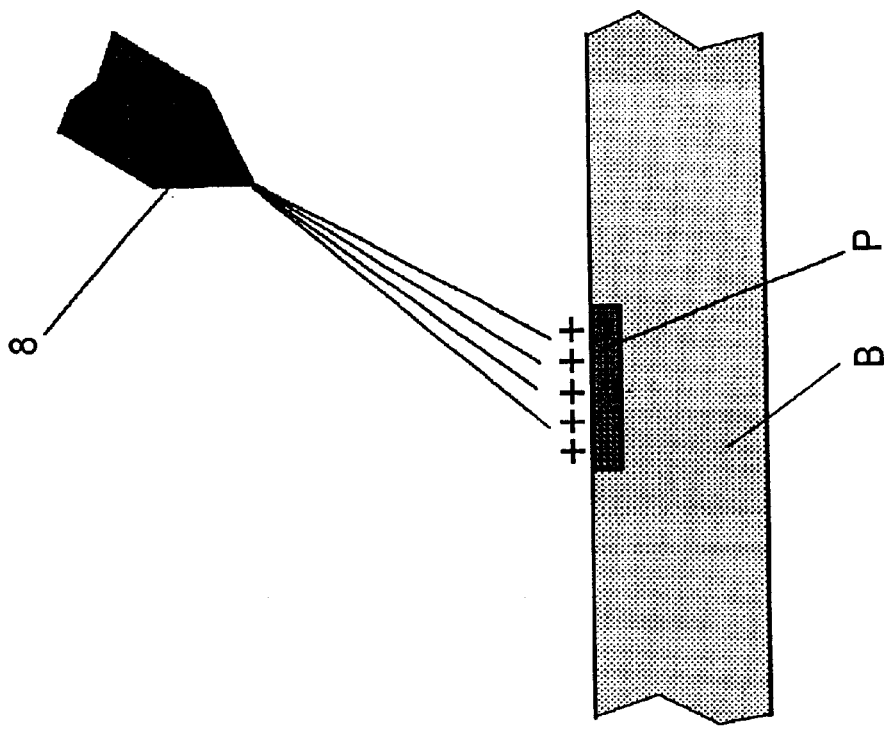
FIGS. 1A and 1B are a drawing to explain the charge up form on the sample surface and its neutralization at the observation utilizing a focused ion beam, FIG. 1A showing a condition of charge up over a wide area, and FIG. 1B showing a condition of charge up in a limited area.
Figure 1A:
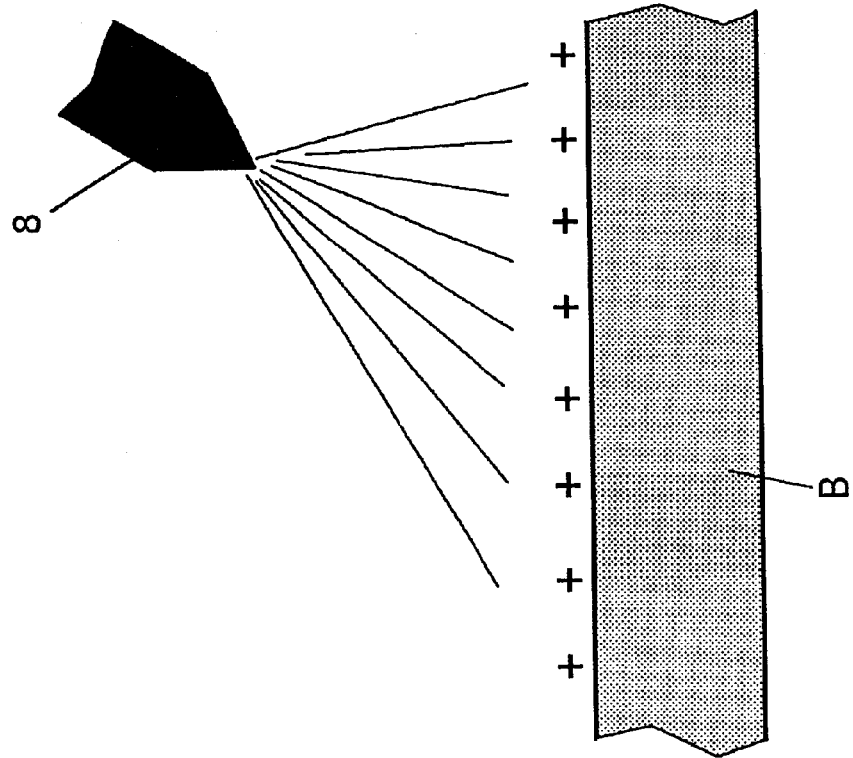
Figure 2:
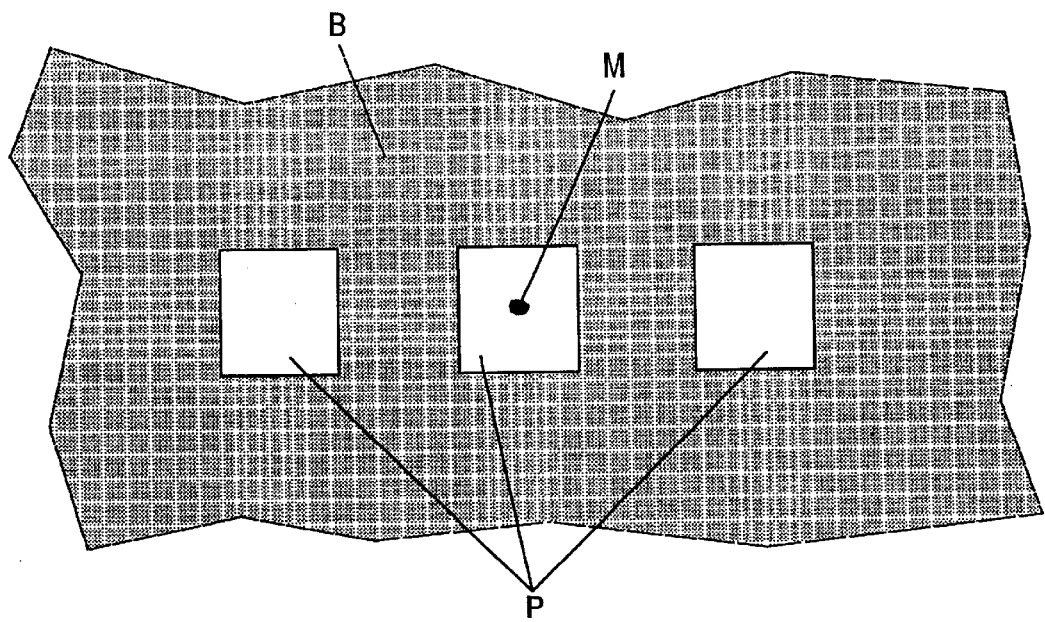
FIG. 2 is a drawing showing an example of observation of the microscopic isolated pattern on the insulating substrate.

The present invention is intended to solve problems such as, when obtaining an image of the sample for the observation by a scanning ion microscope, the sample surface gradually takes charge due to the irradiation of the ion beam, whereby drift is caused in the path of the ion beam. As shown in FIG. 1A, in the case where a wide area of the surface of substrate B is equally charged up, a traditional charge neutralizer can be used to neutralize the charge up by irradiating the area having a diameter of from 300 μm to 5 mm with an electron shower. Accordingly, a clearer drift of the ion beam or a clearer image of the whole pattern can be obtained. However, in the observation for the modification of, for example, defect M of a microscopic isolated pattern P on an insulated layer shown in FIG. 2, there are cases where the surface of the isolated pattern without the space to escape takes on a great amount of charge and the secondary charged particles from the defect part can not be detected as shown in FIG. 1B. To observe more microscopic defects in the microscopic pattern by neutralizing a strong charge in the limited area, irradiation of electrons by focusing a beam having a diameter of 10 μm to 500 μm is deemed to be required. Thus irradiation of electrons from the neutralizer focused in a beam manner is tried, but it can not handle the charge up over a wide area and the problem of drive of the ion beam can not be resolved. As the precision of the position information becomes worse, the ultra-microscopic defect image becomes unclear, and the problem of the image of the large pattern becoming out of focus can not be resolved. Therefore, a charge neutralizer, with a function of wide area irradiation and a function of spot irradiation, with a switchable operation to handle wide area charge up and limited area charge up has been introduced. However, the switching of the operaiton of the charge neutralizer takes a long time to reach a stable operaiton, and so the initial purpose can not be achieved. The present invention realizes a charge neutralizer with a function for wide area irradiation and spot irradiation, in embodiments such as 1 providing two charge neutralizers, 2 scanning an electron beam for wide area charge up and stopping for limited are a charge up, and 3 causing electron irradiation in a beam manner in the center and in a shower manner for the periphery, utilizing a special iris, so that it is capable handling the phenomenon of wide area charge up and the phenomenon of limited area charge up at the same time.

With embodiment ①, when a image becomes unclear due to the charge-up phenomenon while observing the microscope image, either of the two charge neutralizers can be selected according to the manner of charge up. Also, as each charge neutralizer is for exclusive use, both can be used at the same time. Therefore this embodiment is superior in its response. However, as it is necessary to arrange equipment, such as secondary charged particle detectors or gas guns etc., near the sample stage of the focused ion beam device, and to provide a plurality of charge neutralizers, there is a problem that the arrangement of equipment is troublesome.

The embodiment ② does not change the way of focusing the electron beam at the electron optical system using a traditional switching operation, but changes the drive to scan or to stop the same electron beam using a deflector to handle wide area charge up and limited area charge up. Thus a deflector for controlling intensity of the electron beam should be provided for this charge neutralizer, but when switching between wide area irradiation and limited area irradiation, it does not take long to reach the stable state, as it does with the traditional charge neutralizer, and has superior response.

Figure 3:
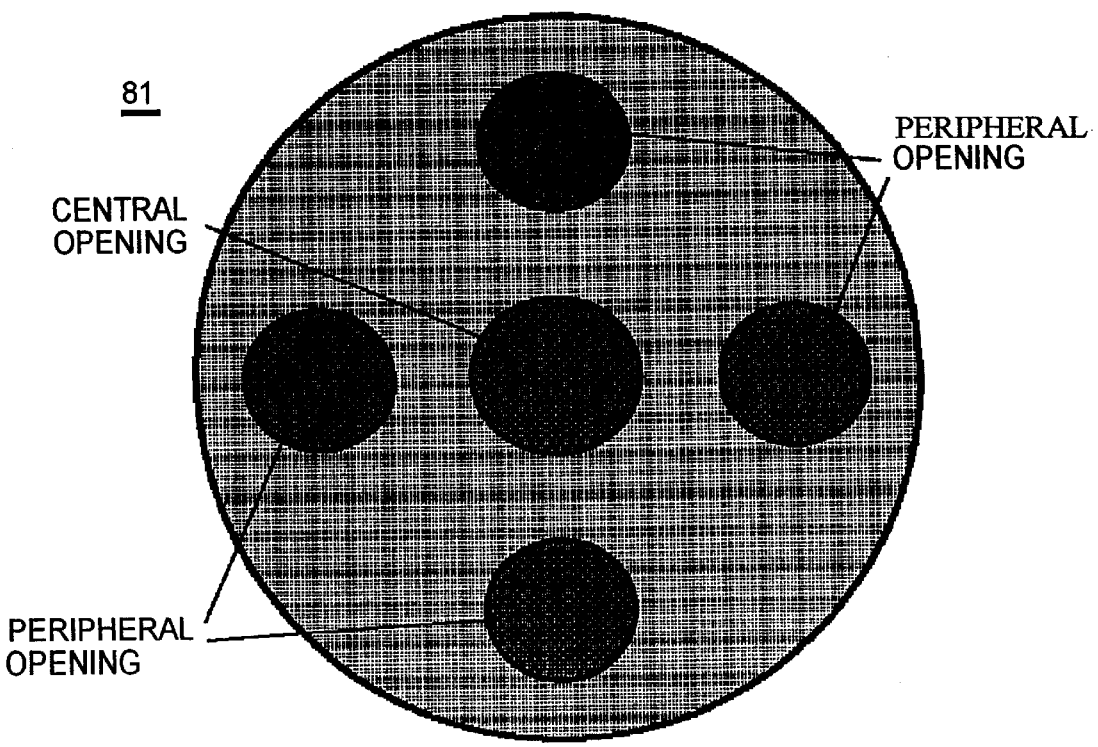
FIG. 3 is a drawing showing the structure of an iris utilized in embodiment ① of the present invention.

The embodiment ③ uses an iris 81, having a central opening to allow an electron beam to pass through and a plurality of openings arranged in the periphery of the central opening as shown in FIG. 3. An electron flow irradiated from the electron gun generally takes a regular distribution in two dimensions, with the electron density being high in the center part, and moving away from the center, the density becomes low. Accordingly, providing an iris such as mentioned above within the electron optical system, the electron beam with high density, having passed through the central opening, will be focused in a beam manner by the above mentioned optical system, and the electron flow with low density, having passed through the plurality of the openings in the periphery, will be irradiated while being scattered by the optical system. This embodiment is characterized by the fact that it utilizes one charge neutralizer, and does not switch between the wide area irradiation and the limited area irradiation, but irradiates both areas at the same time.

Figure 4:
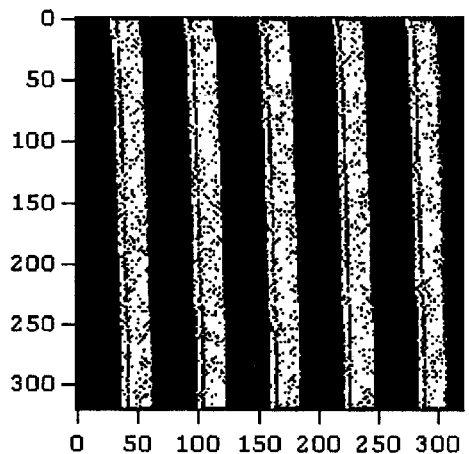
FIGS. 4A and 4B are drawings showing an example of an improvement made by the present invention with respect to image drift due to wide area charge up.
Figure 4:
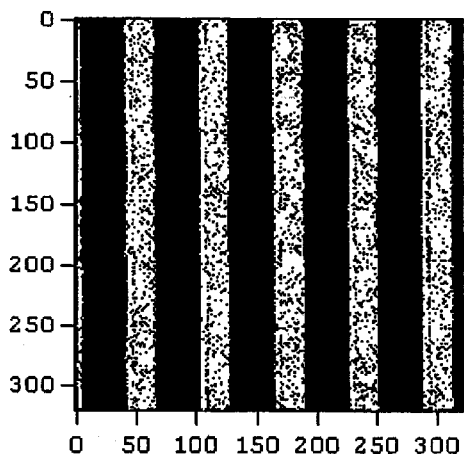

An example of sample observation using the focused ion beam device provided with an electron irradiation means to neutralize wide area charge up and limited area charge up of the present invention is shown below. FIGS. 4A, 4B are a line pattern image showing resolution of the drift of the image by performing electron irradiation to the area much wider than the observation area, when the ion beam is drifting due to charge-up. A is the image before the electron irradiation, and B is the image after the charge-up is resolved by performing the electron irradiation. This image is of a line pattern sample that is a square of 10 μm×10 μm, and the value of the electrical current is 2 nA. The values on the vertical axis and the horizontal axis indicate the number of dots.

Figure 5:
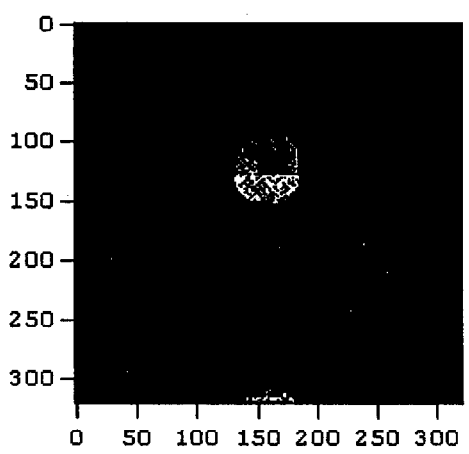
FIGS. 5A and 5B are drawings showing an example of an improvement made by the present invention with respect to lack of image clarity due to limited area charge up.
Figure 5:
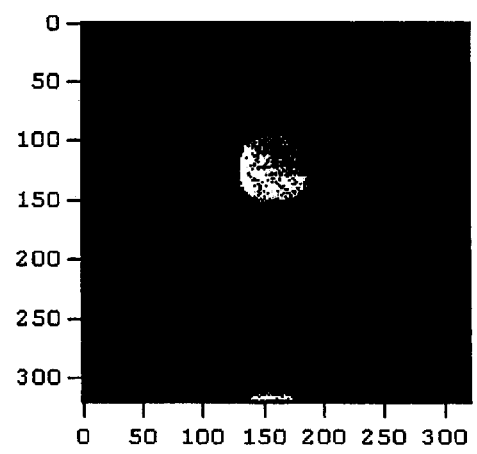
Figure 6:
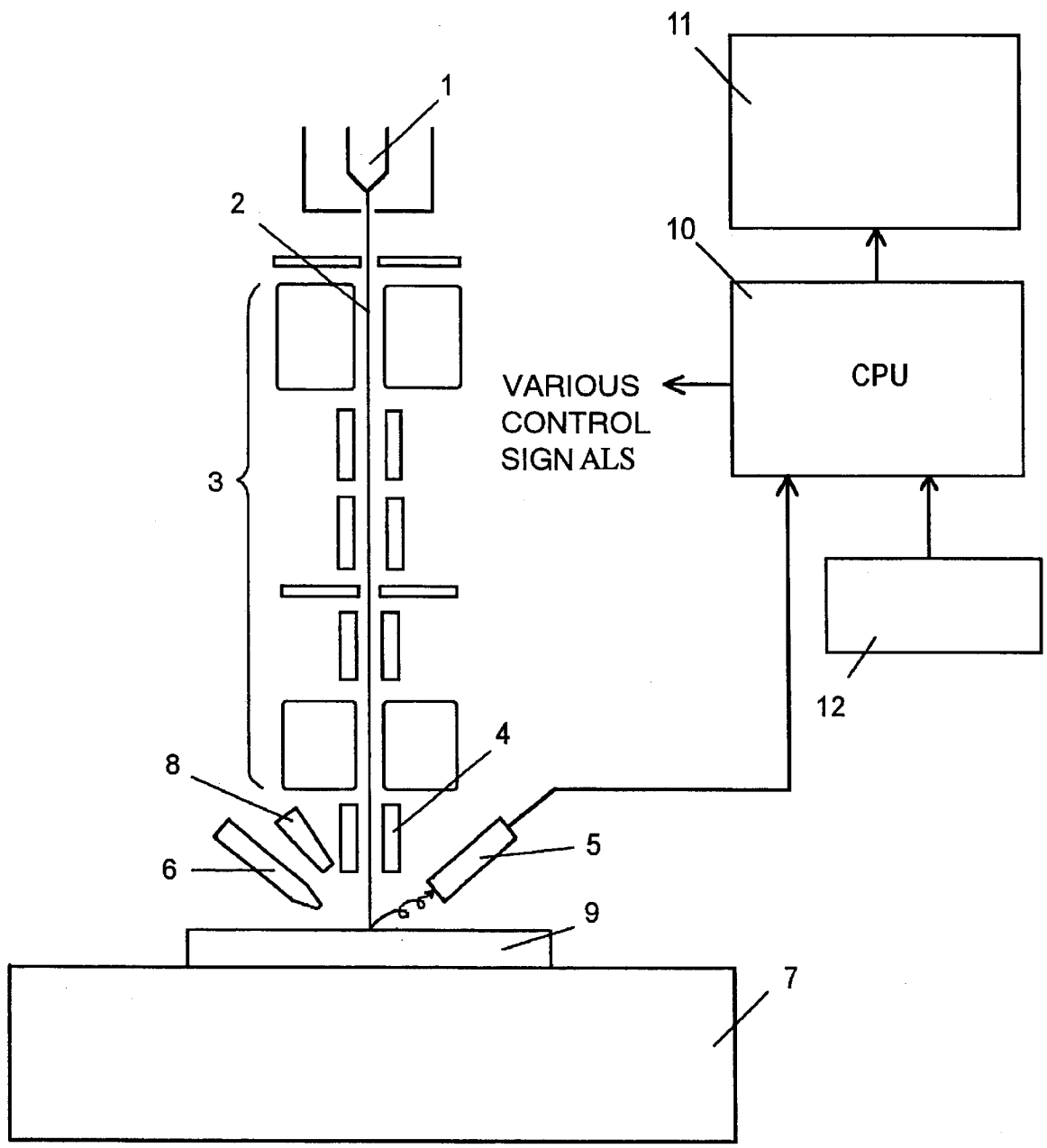
FIG. 6 is a drawing showing basic components of the focused ion beam device.

FIGS. 5A and 5B are an image of an isolated pattern called a "floating island", which shows that the charge-up in a limited area is resolved by irradiating a high density electron beam to the area which slightly exceeds the observation area in the case where the edge of the isolated pattern is out of focus due to the charge-up in the limited area. FIG. 5A is the image before the electron irradiation, and FIG. 5B is the image after the electron irradiation showing that the charge-up is resolved. The image size is also 10 μm×10μ, and the value of the current is 2 nA. Thus, according to the present invention, the electron irradiation for both wide area and limited area can be realized so as to cope effectively with the various types of charge-up.

The present invention provides an electron irradiation means for a focused ion beam device having both a function to irradiate electrons over a wide area and a function to irradiate electrons in a limited area, at the same time. For example, to observe the effects of the isolated conducting pattern of semiconductor devices being more precise and the patterns being more microscopic recently, a wide area electron irradiation function neutralizes the charge up over a wide area, and an appropriate limited area electron irradiation can be used for the area within the microscopic pattern which remains unclear. Therefore an extremely effective charge up neutralization can be performed, so that a vivid image can be obtained.

An embodiment, having a structure with a central opening for passing an electron beam through and a plurality of openings in the periphery of the central opening so as to have both a wide area electron irradiation function and a limited area electron irradiation function at the same time, a function to irradiate a limited area with electrons in a beam manner passing through the central opening, and a function to irradiate over a wide area with scattering electrons passing through the plurality of openings arranged in the periphery of the central opening can be realized. Thus it can promptly cope with wide area charge up and limited area charge up, while being realized in the form of a single charge neutralizer, which does not need so much space.

When employing an electron irradiation means for a focused ion beam device, in which wide area irradiation and limited area irradiation are switched by controlling an electron beam by beam deflection means, such as allowing or stopping an electron beam, it is realized in a form of one charge neutralizer. Therefore it does not require so much space. Moreover, as the switch operation does not change the form of the electron beam and is capable of quick response, it achieves a quick and precise response.

What is claimed is:

1. A focused ion beam apparatus comprising: means for irradiating a sample with an ion beam; and electron irradiation means for neutralizing an electrical charge of the sample caused by the ion beam irradiation, the electron irradiation means having first means for irradiating electrons over a wide area of the sample and second means for irradiating electrons in a local area of the sample.

2. A focused ion beam apparatus according to claim 1; wherein the second means comprises an iris having a central opening to allow an electron beam to pass therethrough, and the first means comprises a plurality of openings surrounding the central opening, such that electrons are irradiated in a local area in a beam manner passing through the central opening, and electrons are irradiated over a wide area in a scattered manner by passing through the plurality of openings surrounding the central opening.

3. A focused ion beam apparatus according to claim 1; wherein the first means comprises a first electron gun for irradiation of the sample with electrons over a wide area, and the second means comprises a second electron gun separate from the first electron gun for irradiation of the sample with electrons in a local area.

4. A focused ion beam apparatus according to claim 1; wherein the electron irradiation means comprises beam deflection means for scanning an electron beam to irradiate electrons over a wide area of the sample, and for stoping the scanning of the electron beam to irradiate a local area of the sample with the electron beam.

5. A focused ion beam apparatus comprising: means for irradiating a sample with an ion beam; and at least one neutralizer for neutralizing electrical charge of the sample caused by ion irradiation, the at least one neutralizer having means for irradiating electrons over a wide area of the sample and means for irradiating electrons onto a local area of the sample at the same time as irradiation of electrons over a wide area of the sample.

6. A focused ion beam apparatus according to claim 5; wherein the neutralizer has an iris with a central opening to allow an electron beam to pass therethrough, and a plurality of openings surrounding the central opening, such that electrons are irradiated in a local area in a beam manner by passing through the central opening, and electrons are irradiated over a wide area in a scattered manner by passing through the plurality of openings.

7. A focused ion beam apparatus according to claim 5; wherein the neutralizer comprises a first electron gun for irradiation of electrons over a wide area of the sample, and a second electron gun for irradiation of electrons onto a local area of the sample.

8. A focused ion beam apparatus according to claim 5; wherein the neutralizer comprises a beam deflector which scans an electron beam to irradiate electrons over a wide area, and which stops scanning the electron beam to irradiate a local area of the sample with the electron beam.

9. A focused ion beam apparatus comprising: an ion beam source for irradiating a local area of a sample surface with a focused ion beam; a first electron source for irradiating electrons onto the local area of the sample surface to neutralize charge-up of the local area; and a second electron source for irradiating electrons over a wide area of the sample surface including the local area to maintain a constant potential across the sample surface.

10. A focused ion beam apparatus according to claim 9; wherein the first electron source comprises a plate having a central opening therethrough to allow electrons to pass therethrough to irradiate the local area of the sample, and the second electron source comprises one or more openings surrounding the central opening to allow electrons to pass therethrough to irradiate the wide area of the sample surface.

11. A focused ion beam apparatus according to claim 9; wherein the first electron source comprises a first electron gun for irradiation of the sample with electrons in the local area, and the second electron source comprises a second electron gun separate from the first electron gun for irradiation of the sample with electrons across the wide area.

12. A focused ion beam apparatus according to claim 9; wherein the first and second electron sources comprise beam deflection electrodes for scanning an electron beam to irradiate electrons over the wide area of the sample surface, and to stop scanning of the electron beam to irradiate the local area of the sample surface with the electron beam.

13. A focused ion beam apparatus according to claim 9; wherein the first and second electron sources irradiate the sample at the same time.

14. A focused ion beam apparatus according to claim 9; further comprising a secondary electron detector for detecting secondary electrons emitted by the sample in response to irradiation with the focused ion beam and outputting a corresponding signal; and image display means for displaying an image of the sample surface based on the output signal of the secondary electron detector.

* * * * *